United States Patent [19]

Marty

[11] Patent Number: 5,336,508
[45] Date of Patent: Aug. 9, 1994

[54] PRESERVATIVE FOR PHARMACEUTICAL PRODUCTS

[75] Inventor: Herbert Marty, Uitikon, Switzerland

[73] Assignee: Similasan Corporation, Kent, Wash.

[21] Appl. No.: 3,835

[22] Filed: Jan. 11, 1993

Related U.S. Application Data

[63] Continuation of Ser. No. 763,341, Sep. 20, 1991, abandoned.

[51] Int. Cl.$^5$ .................. A61K 33/38; A61K 33/14
[52] U.S. Cl. ................................. 424/618; 424/663; 514/912
[58] Field of Search ................ 424/663, 618; 514/912

[56] References Cited

U.S. PATENT DOCUMENTS 4,043,932  8/1977  Fresenius et al. ................. 252/95

OTHER PUBLICATIONS

Brussieux et al., Annales de Pediatrie. 38(9):637–641 (1991).
Gutman et al., Amer J. Ophthal. 65:183–187 (1968).
Hanna et al., Arch Ophthalmol. 92:18–22 (1974).
Moss et al., Arch Ophthalmol. 97:906–907 (1979).
Pifer et al., Scand J Work Environ Health. 15:210–221 (1989).
Schnetkamp et al., J. Membrane Biol. 108:91–102 (1989).
Bartley, Arch Ophthalmol. 110:596 (1992).
Duke-Elder, "Diseases of the Outer Eye, Part II", p. 990 (1965).
Scroggs et al., Cornea. 11(3):264–269 (1992).
Abelson et al., Thimerasol Update. Exerpta. (1982).
Gardner, Optometric Monthly. Nov.:631–635 (1982).
Mondino et al., Survey of Ophthalmol. 26(6):337–344 (1982).
Reitschel et al., Arch Dermatol. 118:147–149 (1982).
Wright et al., Trans ophthalmol Soc UK 102(3):3–6 (1982).
Binder et al., Arch Ophthalmol. 99:87–90 (1981).
Wilson et al., Ophthalmology 88(8):804–809 (1981).
Mondino et al., Arch Ophthalmol. 98:1767–1770 (1980).
Shaw, Contact Lens. 6(3):273–277 (1980).
Wilson, Contact Lens Jnl. 9(9):21–24 (1980).
Morgan, Ophthalmology 86(6):1107–1119 (1979).
Grant, "Toxicology of the Eye" 2nd Ed., 909–918 (1974).
Wallace, "Clinical Ocular Pharmacology", 530–531 (1989).
Skoglund et al., Scand. J. Dent. Res. 99:320–328 (1991).
Ölveti, Contact Dermatitis 24:57 (1991).
Burrows, Int. Dental Jnl. 35(1):30–34 (1986).
Montoya-Cabrera et al., Gaceta Medica de Mexido 127(3):267–270 (1991).
Sau et al., Jnl. Amer. Acad. Dermatol. 25(5):915–919 (1991).
Kanluen et al., Arch. Pathol. Lab Med. 115:56–60 (1991).
Rowens et al., Chest. 99(1):185–190 (1991).
Rosenman et al., Jnl. Occupational Med. 21(6):430–435 (1979).
Rungby, Acta Neuropathol. 37(5) (1990).
Rungby et al., Pharmacology and Toxicoloty 70:205–207 (1992).
Wan et al., Clin. Chem. 37(10):1683–1687 (1991).
Cai et al., Current Eye Research 7(4):341–351 (1988).
Abelson, Ophthalmology Times 12/1:32–33 (1982).

*Primary Examiner*—Zohreh Fay
*Attorney, Agent, or Firm*—Weingarten, Schurgin, Gagnebin & Hayes

[57] ABSTRACT

A pharmaceutical composition comprising at least one active ingredient, a carrier substance and a preservative dissolved in the carrier substance, the preservative comprising sodium silver chloride compound, is disclosed.

12 Claims, No Drawings

PRESERVATIVE FOR PHARMACEUTICAL PRODUCTS

This application is a continuation of application Ser. No. 07/763,341, filed Sep. 20, 1991, now abandoned entitled: PRESERVATION FOR PHARMACEUTICAL PRODUCTS.

BACKGROUND OF THE INVENTION

1. Field of the Invention

The invention refers to a preservative for pharmaceutical products, especially for ophthalmic pharmaceuticals, nasal spray, ear drops and corresponding veterinary products.

Pharmaceutical products in the form of solutions, suspensions or ointments which are applied directly from a container may get in contact with the body fluids of the user or microorganisms of the environment. Therefore, there is a danger of contamination of the product in the container by bacteria contained in the body fluid. On the other hand the use of preservatives in pharmaceuticals is limited in that any interference with the pharmaceutically active ingredients and any noxious effect to the user is to be avoided.

2. Description of the Prior Art

Especially for preserving ophthalmic pharmaceuticals it has been well documented in the literature that benzalkonium chloride, chlorobutanol, thimerosal, methyl and propyl parabens have many drawbacks and disadvantages. The most common complaints included burning, stinging, and irritation upon instillation. Also, there is a 5% to 15% incidence of allergic reactions to these preservatives. Thimerosal has been shown to exhibit an allergic response as high as 20% in some studies. Thimerosal is a mercurial derivative, therefore, has raised concerns for long-term usage as well. As a result of allergic reactions to thimerosal, almost all ophthalmic products that contained thimerosal have had formulation changes to one of the other available preservatives.

Another characteristic of these preservatives is that they have been shown to cause a disruption of the cornea epithelium upon instillation. Documentation via SEM (scanning electron microscopy) has demonstrated these epithelial changes in the literature.

Obviously, a lot of other preservative substances are known for several purposes and applications. Among them a sodium silver chloride compound has been used for sterilizing water, especially drinking water, and other aqueous solutions as e.g. homeopathic solutions.

SUMMARY OF THE INVENTION

Hence, it is an object of the invention to provide a preservative for use in a wide range of pharmaceutical substances and compositions, i.e. substances containing pharmaceutically active ingredients as e.g. antibiotics, anti-inflammatories or anti-infectives etc. and which in use may be contaminated by body fluids of the user or microorganisms of the environment.

It is a further object of the invention to provide a preservative for use in pharmaceuticals which preservative is chemically inert towards the major pharmaceutically active ingredients and has a high bacteriocidal and bacteriostatic effect against possible contaminations in pharmaceuticals.

Still another object of the invention is to provide a preservative for use in pharmaceuticals which is harmless for the user of the pharmaceuticals and does not interfere with the medical treatment.

These objects are achieved by using a sodium silver chloride compound as a preservative in pharmaceutical products. Though, as already mentioned the sterilizing effect of this substance in water was known as such, it surprisingly has been found that this substance is especially advantageous as a preservative in pharmaceuticals, especially ophthalmic drugs, nasal sprays, ear drops and corresponding veterinary products and therefore is suited to replace the prior used substances thereby avoiding the above mentioned problems, especially allergic reactions to the known preservatives in pharmaceuticals.

It is sufficient to add an amount of 0.0005 to 0.1 weight % of sodium silver chloride compound to the pharmaceutical composition to be preserved in order to keep it sterile for the time of use.

DESCRIPTION OF THE PREFERRED EMBODIMENTS

The invention will be better understood and objects other than those set forth above will become apparent when consideration is given to the following detailed description thereof.

The following examples of pharmaceuticals in which a sodium silver chloride compound salt is used as a preservative mainly refer to ophthalmic pharmaceuticals in the form of solutions, suspensions and ointments. The drugs and drug categories as such are known to the man skilled in the art and the invention is not limited to these drug categories. Sodium silver chloride compounds used in the invention are known as such.

Preferably this sodium silver chloride compound contains $Ag^+$-ions replacing part (in the range of 1%) of the $Na^+$-ions in the NaCl basis, so that there is an excess of NaCl which allows on one hand more accurate dosing and on the other hand provides the necessary amount of effective reagent.

It has been found in sterility tests that the sodium silver chloride compound in concentrations of 1 to 2 mg/100 ml is effective against the following microorganismus:

*Escherichia coli* ATCC 8739
*Pseudomas aeruginosa* ATCC 9027
*Staphylococcus aureus* ATCC 6538
*Candida albicans* ATCC 10231
*Aspergillus niger* ATCC 16404

The test arrangements were in accordance with USP XXI.

EXAMPLE 1

Antibiotics

An ophthalmic antibiotic in the form of a solution or a suspension contains 0.001 weight % of sodium silver chloride complex as preservative. The active agent may be a single ingredient (gentamicin, tobramycin, ofloxacin), a combination of ingredients ( neomycin/-polymyxin, gramicidin), a single ingredient with steroids (gentamicin, prednisolone acetate) or combinations with steroids (neomycin, polymyxin/dexamethasone). In the case of eye drops containing tobramycin as a single active ingredient the composition comprises: 0.3 weight % tobramycin ( active ingredient ); 0.001 weight % sodium silver chloride compound (preservative); excip. ad collyrium tamponat. The indications are bacterial infections of the eye.

EXAMPLE 2

Anti-Allergy

An ophthalmic anti-allergic-composition in the form of a solution or suspension comprises as active agents 0.5 weight % of antazolin. sulfuric. and 0.025 weight % of naphazoline. nitric. As preservative 0.001 weight % of sodium silver chloride compound is provided. Indications are allergic affections of the conjunctiva.

EXAMPLE 3

Anti-glaucoma

An anti-glaucoma preparation in liquid form comprises: pilocarpine hydrochloride ( 5 mg ) as active agent: hydroxypropylmethylcellulose; sodium silver chlorid compound (0.01 mg) as preservative; excip. ad collyr. ad 1 ml. Other anti-glaucoma ophthalmic products include epinephrine, dipivefrin, carbachol. Other major categories include: Prostaglandins, topical carbonic Anhydrase Inhibitors, BetaBlockers, ACE and Renin Inhibitors, Calcium Channel Blockers, Forskolln and Analogues. These products are used topically for lowering intraocular pressure and will benefit from use of sodium silver chloride compound as a preservative.

EXAMPLE 4

Anti-Herpetic/Anti-Viral Agents

Idoxurin is an active agent for use in eye drops (0.1%) or ointments (0.25%) and is effective as an antiherpetic composition. The composition further comprises 0.001 weight % of sodium silver chloride compound as a preservative.

EXAMPLE 5

Anti-Infectives

As ophthalmic anti-infective sodium sulfacetamide is known as single ingredient in eye drops (10%). The solution is preserved by sodium silver chloride compound (0.001%). Other anti-infective eye drops may comprise combinations of ingredients or a single ingredient with steroids. An example for the last mentioned type is sodium sulfacetamide (10%)/prednisolone (0.25%) which also can be preserved by 0.001 weight % of sodium silver chloride compound.

EXAMPLE 6

Anti-inflammatories

Dexa-methasone is a known anti-inflammatory agent. A pharmaceutical composition in the form of eye drops contains dexamethasone ( 0.1% ), hydroxypropylmethylcellulose (0.5%), sodium silver chloride compound as preservative (0.001%) and excip. ad collyrium tamponat.

EXAMPLE 7

Artificial Tears/Ocular Lubricants

As can be seen from the above examples, several pharmaceutical compositions comprise hydroxypropylmethylcellulose. This is a substance with abirritant effect to the eyes. The preservative of the invention can be used with this substance in artificial tear compositions comprising e.g. hydroxypropyl-methylcellulose (1%); sodium silver chloride compound (0.001%); excip. ad collyrium tamponat.

EXAMPLE 8

Contact Lens Solutions

Contact lens solutions are isotonic solutions used for cleaning and desinfecting contact lenses and for soaking and wetting the same. In these isotonic solutions the preservative of the invention can be contained as a bacteriostatic agent in a concentration of 0.001 to 0.002 weight %.

EXAMPLE 9

Decongestants

Phenylephrine HCl (0.1%–10%) is an example for a known decongestant ophthalmic agent. A decongestant composition in the form of eye drops contains tetrahydrazoline or phenylephrine HCl (0.12%), hydroxypropyl-methylcellulose (0.5% ), sodium silver chloride complex (0.001% ) as preservative and excip. ad collyrium tamponat.

EXAMPLE 10

Diagnostic Agents

Diagnostic ophthalmic agents are used for a diagnostic dilatation of the pupil of the eye, which e.g. can be effected by tropicamide (0.5%) in the form of eye drops. As a preservative sodium silver chloride compound (0.001%) is added.

EXAMPLE 11

Hypertonic Solutions

Hypertonic saline ointments and solutions with NaCl concentrations of 2 to 5% are used e.g. for the treatment of edema of the cornea. Since sodium silver chloride compound is NaCl based it is especially suited as a preservative for such compositions at a concentration of 0.001% to 0.002%.

EXAMPLE 12

Irrigation Solutions

Ophthalmic irrigation solutions are sterile balanced salt solutions for the external irrigation of the eye. The sterility is maintained by sodium silver chloride complex. A irrigation solution e.g. contains: sodium chloride (0.64% ), potassium chloride (0.075% ), calcium chloride (0.048% ), magnesium chloride (0.03% ), sodium acetate (0.39%), sodium citrate (0.17%), sodium silver chloride compound (0.001% ) and purified water.

EXAMPLE 13

Topical Anesthetics

Topical anesthetics are used for surface anesthesia in ophthalmology. As the active ingredient proparacaine (proxymetacaine-hydrochloride) is used in a concentration of 0.5% in combination with sodium silver chloride compound (0.001%) as preservative in excip. ad collyrium tamponat.

As already mentioned above sodium silver chloride compound can be used also as preservative in nasal spray or ear drops, which during their application may be contaminated in the container by body fluids of the user.

The preceding examples illustrate the wide range of application of sodium silver chloride compound for the preservation of pharmaceutical products which makes it suited to generally replace a lot of known preservatives for drugs especially for ophthalmic drugs.

While there are described present preferred embodiments of the invention, it is to be understood that the invention is not limited thereto, but may be otherwise variously embodied and practiced within the scope of the following claims.

I claim:

1. A pharmaceutical composition comprising a therapeutically effective amount of at least one active ingredient, a carrier substance and a preservative dissolved in said carrier substance, said preservative comprising sodium silver chloride compound.

2. The pharmaceutical composition of claim 1, wherein said at least one active ingredient is selected from the group consisting of an antibiotic agent, an anti-allergy agent, and anti-glaucoma agent, an anti-herpetic agent, and anti-infective agent, an anti-inflammatory agent, a decongestant agent and a topic anesthetic agent.

3. The pharmaceutical composition of claim 1, wherein said active ingredient is a diagnostic agent for diagnostic dilatation of the pupil.

4. The pharmaceutical composition of claim 1, wherein said active ingredient is NaCl in a hypertonic concentration.

5. The pharmaceutical composition of claim 1 for ophthalmic use as artificial tears.

6. The pharmaceutical composition of claim 1 for ophthalmic use as contact lens solution.

7. The pharmaceutical composition of claim 1 for ophthalmic use as topical anesthetic.

8. The pharmaceutical composition of claim 1 for ophthalmic use as diagnostic agent.

9. The pharmaceutical composition of claim 1, wherein said sodium silver chloride compound comprises a NaCl basis in which part the $Na^+$-ions are replaced by $Ag^+$-ions.

10. The pharmaceutical composition of claim 9 wherein about 1% of the $Na^+$-ions are replaced by $Ag^+$-ions.

11. The pharmaceutical composition of claim 10, wherein said sodium silver chloride compound is provided in a concentration from 0.0005 to 0.1 weight %.

12. The pharmaceutical composition of claim 1, wherein said carrier is a solution, suspension or ointment.

* * * * *